United States Patent
Eltorai et al.

(10) Patent No.: US 11,596,772 B2
(45) Date of Patent: Mar. 7, 2023

(54) ANTIMICROBIAL LIGHT-EMITTING PERCUTANEOUS SITE DRESSING

(71) Applicant: Lumen Catheters, LLC, Marlborough, MA (US)

(72) Inventors: Adam E. M. Eltorai, Marlborough, MA (US); Walter Shunaula, Shelton, CT (US); Danial Ferreira, Shelton, CT (US); Paul DiCesare, Shelton, CT (US); Ronald Green, Shelton, CT (US)

(73) Assignee: Lumen Catheters, LLC, Marlborough, MA (US)

( * ) Notice: Subject to any disclaimer, the term of this patent is extended or adjusted under 35 U.S.C. 154(b) by 0 days.

(21) Appl. No.: 17/665,965

(22) Filed: Feb. 7, 2022

(65) Prior Publication Data
US 2022/0249808 A1    Aug. 11, 2022

Related U.S. Application Data

(60) Provisional application No. 63/146,697, filed on Feb. 7, 2021.

(51) Int. Cl.
| | |
|---|---|
| *A61M 25/02* | (2006.01) |
| *A61M 25/06* | (2006.01) |
| *A61L 2/26* | (2006.01) |
| *A61F 13/00* | (2006.01) |
| *A61N 5/06* | (2006.01) |

(Continued)

(52) U.S. Cl.
CPC .............. *A61M 25/02* (2013.01); *A61L 2/26* (2013.01); *A61M 25/0606* (2013.01); *A61F 2013/00412* (2013.01); *A61L 2/0047* (2013.01); *A61L 2202/11* (2013.01); *A61M 2025/0206* (2013.01); *A61M 2025/0246* (2013.01); *A61M 2025/0266* (2013.01); *A61M 2039/0285* (2013.01); *A61M 2039/167* (2013.01); *A61M 2205/053* (2013.01);
(Continued)

(58) Field of Classification Search
CPC .............. A61M 25/02; A61M 25/0606; A61M 2025/0206; A61M 2025/0246; A61M 2025/0266; A61M 2039/0285; A61M 2039/167; A61M 2205/053; A61L 2/26; A61L 2/0047; A61L 2202/11; A61N 5/0624; A61N 2005/0661; A61N 2005/0651; A61N 2005/0666; A61N 2005/0645; A61F 2013/00412
USPC ......................................................... 604/289
See application file for complete search history.

(56) References Cited

U.S. PATENT DOCUMENTS

| | | |
|---|---|---|
| 5,487,895 A | 1/1996 | Dapper et al. |
| 5,833,665 A | 11/1998 | Bootman et al. |

(Continued)

*Primary Examiner* — Kiet T Nguyen
(74) *Attorney, Agent, or Firm* — Armis IP Law, LLC

(57) ABSTRACT

An antimicrobial light dressing device, system and method for a percutaneous treatment that bathes a treatment region around the percutaneous insertion with an antibacterial illumination source for preventing pathogens around the insertion from entering via the dermal puncture created by the insertion. The antimicrobial light dressing device combines a circumferential body centered around the insertion, and an arrangement of LEDs around the body that focus the light around the insertion and onto a therapeutic region of the insertion. An opening in the circumferential body has an articulated protrusion for offsetting a medicinal vessel such as an IV tube off the skin surface to avoid blocking light to an area under the vessel.

27 Claims, 6 Drawing Sheets

(51) Int. Cl.
*A61L 2/00* (2006.01)
*A61M 39/16* (2006.01)
*A61M 39/02* (2006.01)

(52) U.S. Cl.
CPC .... *A61N 5/0624* (2013.01); *A61N 2005/0661* (2013.01)

(56) References Cited

U.S. PATENT DOCUMENTS

| | | | |
|---|---|---|---|
| 7,834,328 B2* | 11/2010 | Redmond | A61L 2/10 250/455.11 |
| 8,197,087 B2* | 6/2012 | Sobue | A61M 1/28 362/249.02 |
| 8,969,649 B2 | 3/2015 | Leibowitz et al. | |
| 10,667,956 B2 | 6/2020 | Holten et al. | |
| 2006/0004317 A1* | 1/2006 | Mauge | A61M 27/006 604/8 |
| 2012/0053512 A1* | 3/2012 | Muse | A61M 39/16 604/20 |
| 2017/0027720 A1* | 2/2017 | Pedtke | A61F 2/78 |

* cited by examiner

ANTIMICROBIAL LIGHT-EMITTING PERCUTANEOUS SITE DRESSING

RELATED APPLICATIONS

This patent application claims the benefit under 35 U.S.C. § 119(e) of U.S. Provisional Patent App. No. 63/146,697, filed Feb. 7, 2021, entitled "ANTIMICROBIAL LIGHT DRESSING DEVICE," incorporated herein by reference in entirety.

BACKGROUND

Intravenous (IV) access is a common medical practice for direct fluid communication with blood vessels. A sharp, rigid member such as a needle is inserted into a dermal (skin) surface for piercing the dermal surface and extending into a blood vessel, or alternatively into a tissue region. While often employed for medicinal delivery, an sharp, inserted member may also be employed for fluid removal, such as testing samples and relief of excess fluid buildup. Whatever the therapeutic motivation, such a breach in the epidermal surface presents a pathway for infection from pathogens traversing the breached skin barrier

SUMMARY

Configurations herein are based, in part, on the observation that percutaneous delivery of medication is an effective medium for medicinal treatment directly to blood or tissue, which allows the medication to be quickly delivered to a specific region. In the case of general bloodstream delivery, it avoids degradation that can occur by oral administration which must pass via the gastrointestinal barrier. Unfortunately, conventional approaches to percutaneous delivery, typically via a needle or similar insertion member, suffer from the shortcoming that they pose an infection risk from a breach of the natural dermal (skin) barrier which guards against infiltration of pathogens. Typically, an antimicrobial substance is applied around the insertion point of the needle, however such chemical based approaches generally have diminishing effects over time, and need repeated applications for continued effectiveness.

Accordingly, configurations herein substantially overcome the shortcomings of chemical and topical approaches by providing an antimicrobial light dressing device, system and method for a percutaneous treatment that bathes a treatment region around the percutaneous insertion with an antibacterial illumination source for preventing pathogens around the insertion from entering via the dermal puncture created by the insertion. The antimicrobial light dressing device combines a circumferential body centered around the insertion, and an arrangement of LEDs around the body that focus the light around the insertion and onto a therapeutic region of the insertion. An opening in the circumferential body has an articulated protrusion for offsetting a medicinal vessel such as an IV tube off the skin surface to avoid blocking light to an area under the vessel. The result is a 360 degree coverage of antimicrobial light around the percutaneous insertion as the medicinal vessel contacts the skin surface only at the insertion point in the center of the treatment region.

BRIEF DESCRIPTION OF THE DRAWINGS

The foregoing and other objects, features and advantages of the invention will be apparent from the following description of particular embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION

A device for the dressing of wounds and insertion sites of percutaneous and drug delivery devices provides circumferential protection of a wound or insertion site of a percutaneous or drug delivery device. In particular, the device is an integrated dressing for vascular and non-vascular percutaneous medical devices (e.g., IV catheters, central venous lines, arterial catheters, dialysis catheters, peripherally inserted coronary catheters, mid-line catheter, drains, chest tubes, externally placed orthopedic pins, ventricular assist device drivelines, and epidural catheters) comprising an adhesive dressing and an antimicrobial light source, such as visible light, far UVC light, and any suitable electromagnetic emission of a therapeutically beneficial wavelength. The dressing device reduces infection risk from vascular and non-vascular percutaneous medical devices by providing sufficient tissue-safe antimicrobial light at a wound or insertion site.

Figure 1:
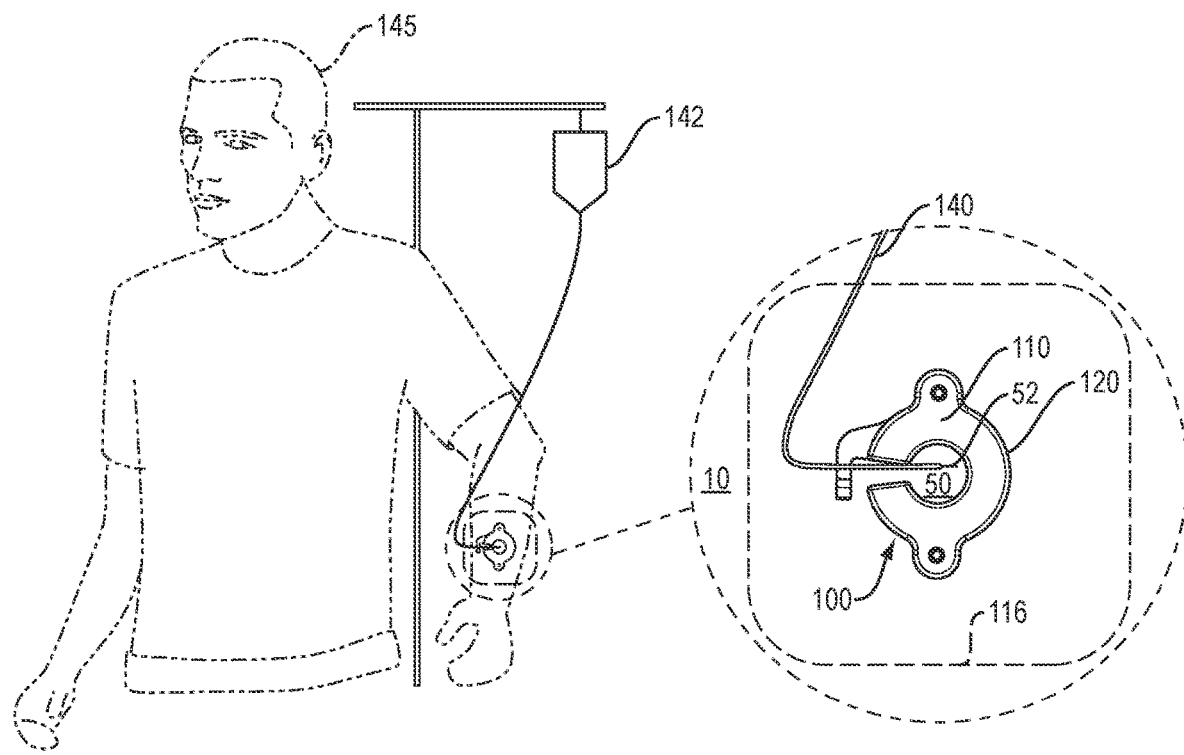
FIG. 1 is a context view of a medical treatment environment suitable for use with configurations herein.

FIG. 1 is a context view of a medical treatment environment suitable for use with configurations herein. Referring to FIG. 1, an antimicrobial epidermal device 100 includes a circumferential light-emitting body 110 configured for adhesion around a percutaneous insertion site 52 for directing therapeutic light at the percutaneous insertion site while permitting unobstructed passage of a medication vessel 140 to the percutaneous insertion site 52. The medication vessel emanates from a fluidic source 142 of medication or other liquid, such as an IV (Intravenous) bag. The percutaneous insertion site 52 defines a surrounding treatment region 50, typically on an arm of a patient 145 because of ease of IV access, however any suitable epidermal region may be selected for the percutaneous insertion site.

In the antimicrobial epidermal device 100, the circumferential body 110 is adapted for epidermal placement on the treatment region 50 of a larger epidermal surface 10. Placement is based on a central void 120 in the circumferential body for epidermal access and alignment generally over the insertion site 52. The circumferential body 110 includes an illumination source disposed for emitting a therapeutic light on the treatment region 50 defined by the central void 120. An adhesive member 116, such as a patch or bandage, adheres the circumferential body 110, vessel 140 and a percutaneous penetration member such as a needle to the epidermal area around the treatment region 50.

Figure 2:
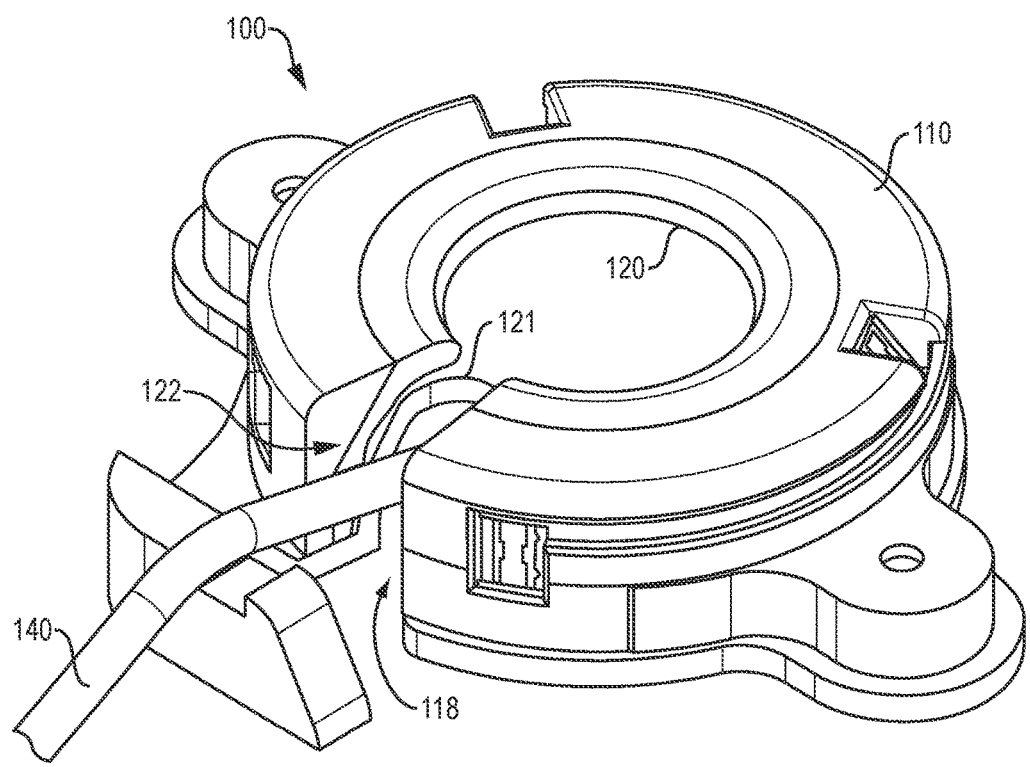
FIG. 2 is a perspective view of the medical device for antimicrobial light treatment of a percutaneous insertion site.

FIG. 2 is a perspective view of the medical device of FIG. 1 for antimicrobial light treatment around a percutaneous insertion site 52. FIG. 2 shows the central void 120 accessible by a vessel gap 122 in the circumferential body 110 for passage of the medication vessel 140 to a penetration or insertion member defining the insertion site 52. The treatment region 50 is defined by a radius around the insertion site roughly centered within the circumferential body. In the example of FIG. 2, the central void 120 remains covered by an insert 121 except at the vessel gap 122 for permitting vessel access into an illumination cavity 118.

Figure 3A:
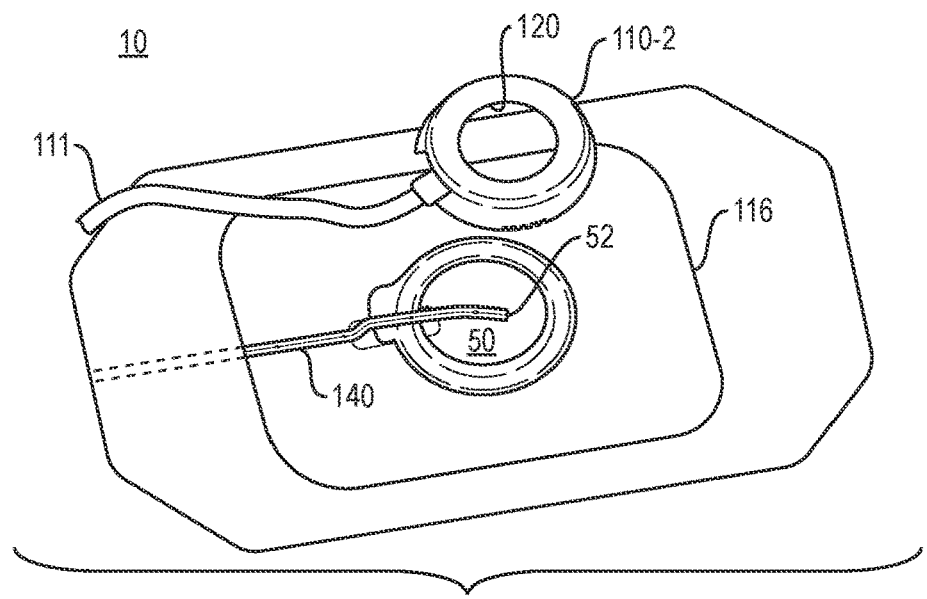
FIGS. 3A-3C show engagement of the device of FIG. 2 with a treatment region defined by the percutaneous insertion site.
Figure 3B:
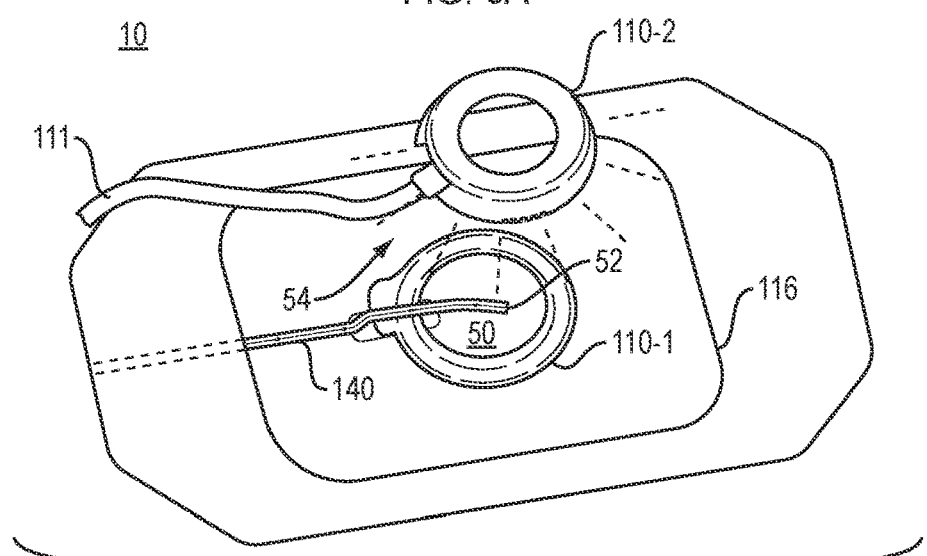
Figure 3C:
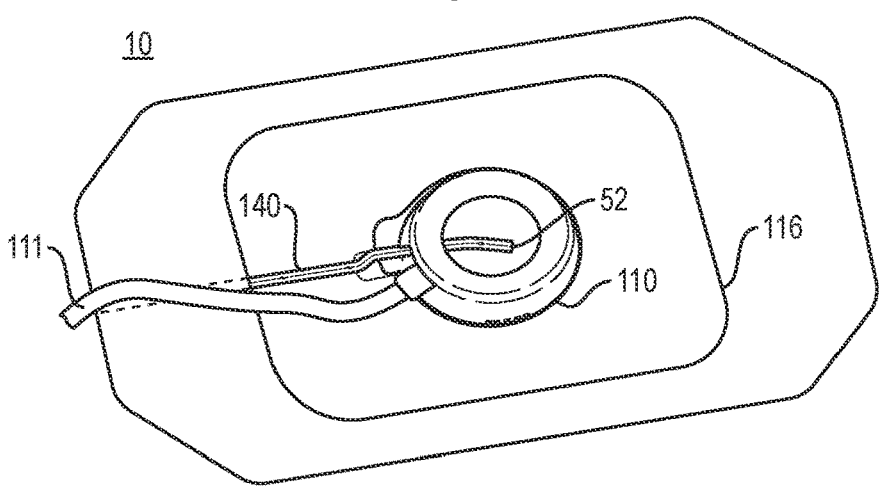

FIGS. 3A-3C show engagement of the device of FIG. 2 with a treatment region defined by the percutaneous insertion site. In a particular configuration, the device may be combined with an adhesive member 116 such as a sheet, patch or bandage for providing a system of secure attachment of the illumination source to the percutaneous insertion site. Referring to FIGS. 1-3C, the circumferential body 110 is disposed on an epidermal surface 10, in conjunction with an adhesive member 116. The adhesive member 116 has an adhesive attraction to the epidermal surface 10 and extends over the treatment region 50 and is disposed for securing the circumferential body 110 and a treatment vessel 140 directed to the central void 120. The adhesive member my include a securement or fixation dressing having adhesive and therapeutic or antimicrobial properties. The securement or fixation dressing is disposed between the circumferential body 110 and the epidermal surface 10, The circumferential body is therefore disposed in place by the underlying securement or fixation dressing/patch, and substantially centered around the insertion site.

The configuration of FIG. 3 shows a two-part configuration of the device. The circumferential body 110 further includes a distal layer 110-2 including a power connection 111 for powering an illumination source such as one or more LED elements and a proximate layer 110-1 having a translucent surface, in which the LED elements are disposed within the distal layer 110-2 for directing the therapeutic light onto the treatment region 50.

The proximate layer 110-1 engages with the adhesive member 116, which may be integrated as an adhesive whole or applied in separate phases. In the configuration of FIGS. 3A-3C, the adhesive member 116 may reside between the proximate layer 110-1 and distal layer 110-2. The adhesive member 116 secures the insertion member at the insertion site 52 alone with the medication vessel 140, shown in FIG. 3A. The treatment region 50 is defined by a radius around the dermal insertion site 52, where the insertion site 52 provides the dermal access for medical intervention through the skin by a sharp, piercing structure.

In FIG. 3B, the distal layer 110-2 approaches the secured, proximate layer 110-1. The distal layer 110-2 may already be emitting light 54 onto the treatment region 50. In FIG. 3C, the distal layer 110-2 engages the proximate portion 110-2 to form the full circumferential member 110, and encapsulates an illumination cavity, discussed further below.

Figure 4A:
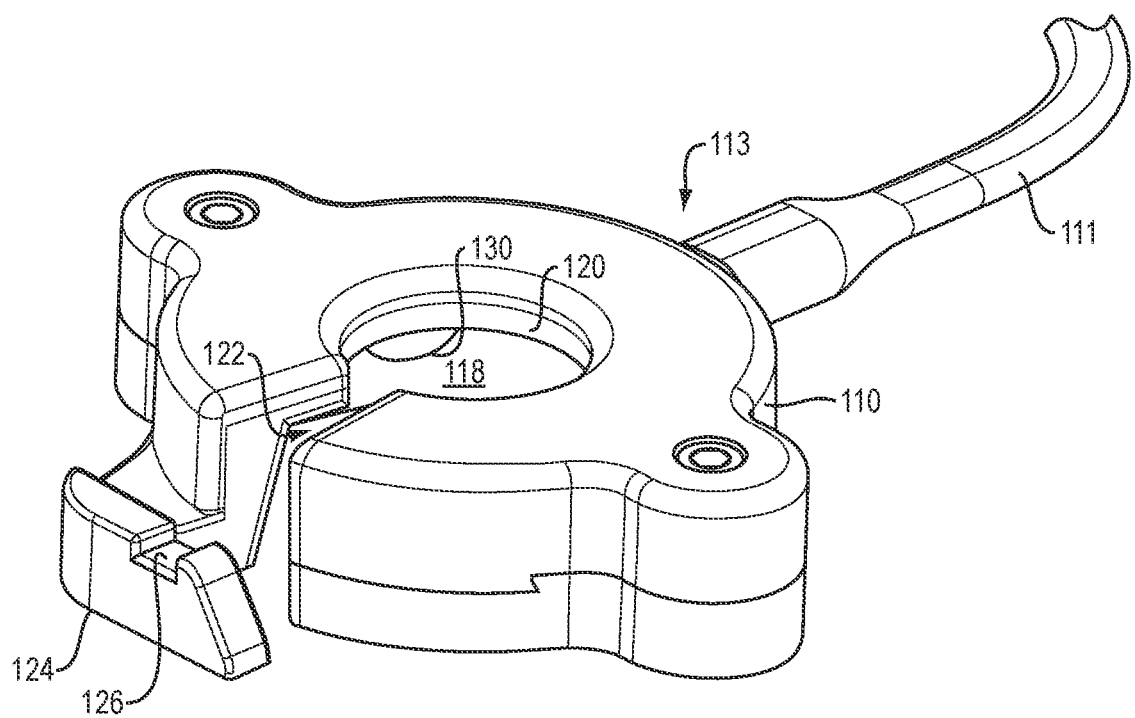
FIGS. 4A-4B show perspective views of a central void in the device of FIGS. 1-3c.
Figure 4B:
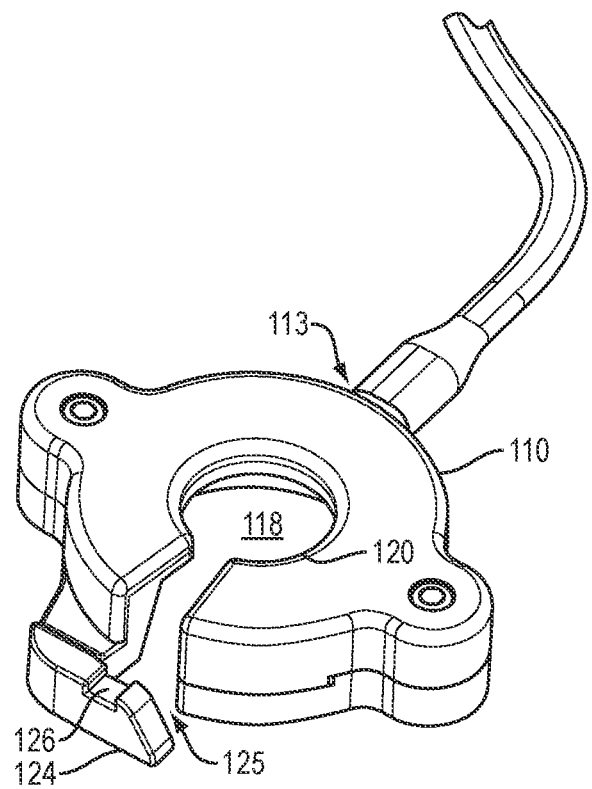

FIGS. 4A-4B show perspective views of a central void 120 in the device of FIGS. 1-3c. Referring to FIGS. 1-4B, upon adherence and proper administration, the circumferential body 110 adheres to the epidermal surface 10 with the central void 120 roughly centered on the insertion site 52. An illumination source 130 includes at least one LED element defining the illumination source, in which the LED element emits a wavelength based on an antimicrobial effect. The central void 120 has a size based on a treatment vessel 140 size and clearance over the insertion site 152. The treatment vessel 140 has an attachment to the insertion member such as a needle for a percutaneous insertion under the central void. The vessel extends through the vessel gap 122 and through the central void 120 or at least through the gao 122 and into the illumination cavity 118.

A power connection 113 receives the power supply 111 on the circumferential body 110. The power supply couples to the illumination source 130 and is adapted for receiving an electrical source for powering the illumination source, such as an external USB, batteries, AC or similar AC or DC source based on the electrical requirements of the illumination source 30. A discontinuity in the circumferential body defines the vessel gap 122 for accommodating the treatment vessel 140. The treatment vessel 140 couples to the percutaneous insertion member in the treatment region 50 under the central void 120. Routing of the treatment vessel 140 is provided by a protrusion 124 extending outward from the circumferential body. The protrusion 124 has an elevated surface 126 disposed away from the epidermal surface 10, such that the elevated surface 126 is adjacent the vessel gap 122 for directing the treatment vessel at an offset distance from the dermal surface 10. Elevation of the treatment vessel 140 above the skin avoids a shadow from the light and instead allows a shadowed region 125 to be reached by light from the illumination source 130 rather than being shaded or obscured by the vessel 140 from reaching the skin at the shadowed region.

Figure 5:
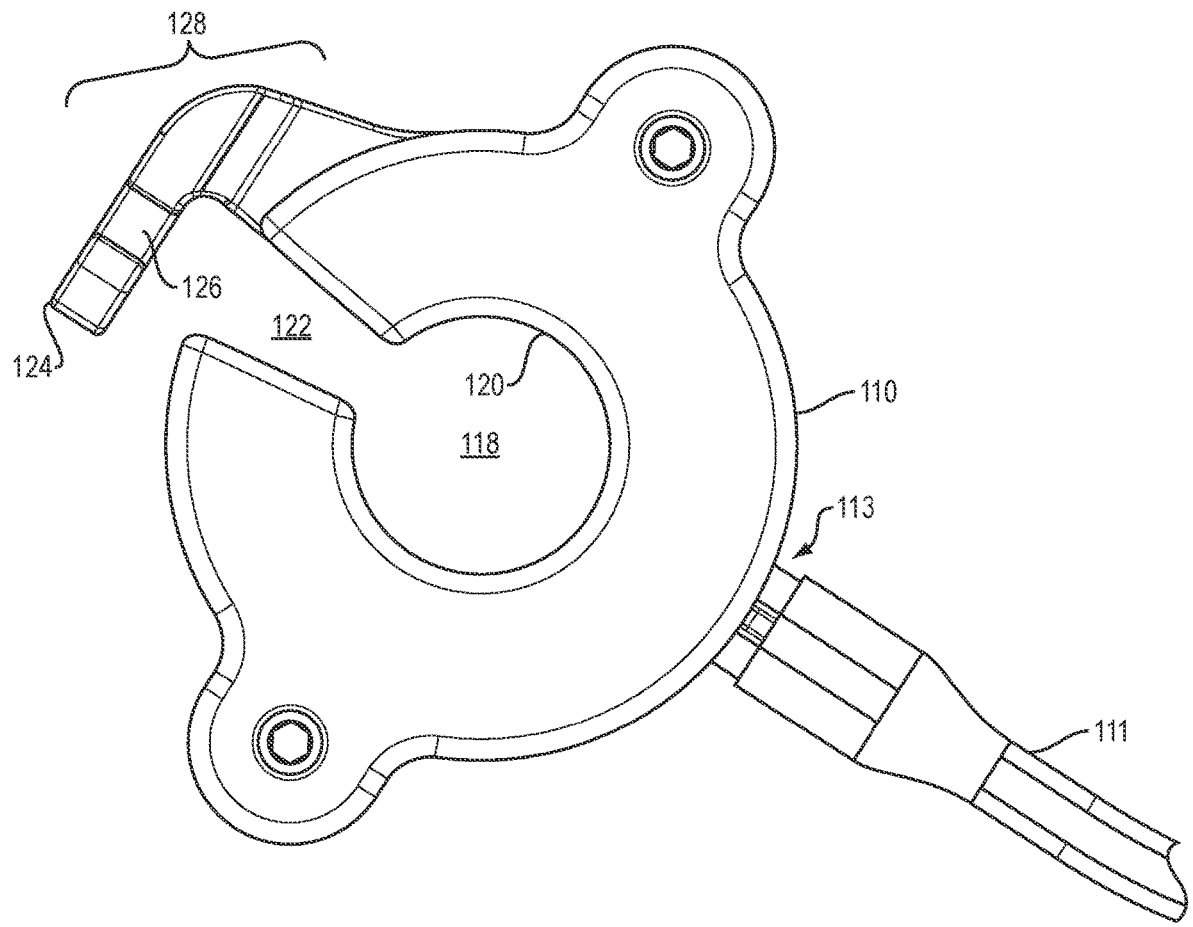
FIG. 5 shows a plan view of the device of FIGS. 1-4B.

FIG. 5 shows a plan view of the device of FIGS. 1-4B. Referring to FIGS. 1-5, the vessel gap 122 is an opening or passage in the circumferential body 110. A lateral extension 128 extends radially from the circumferential body 110 adjacent the vessel gap 122, and turns toward the gap 122 to provide the elevated surface 126 residing on the protrusion 124. The elevated surface 126 is disposed on a path towards the central void 120 for receiving a treatment vessel 140 disposed on the path for fluidic delivery to an insertion site 52 in the treatment region 50.

Figure 6:
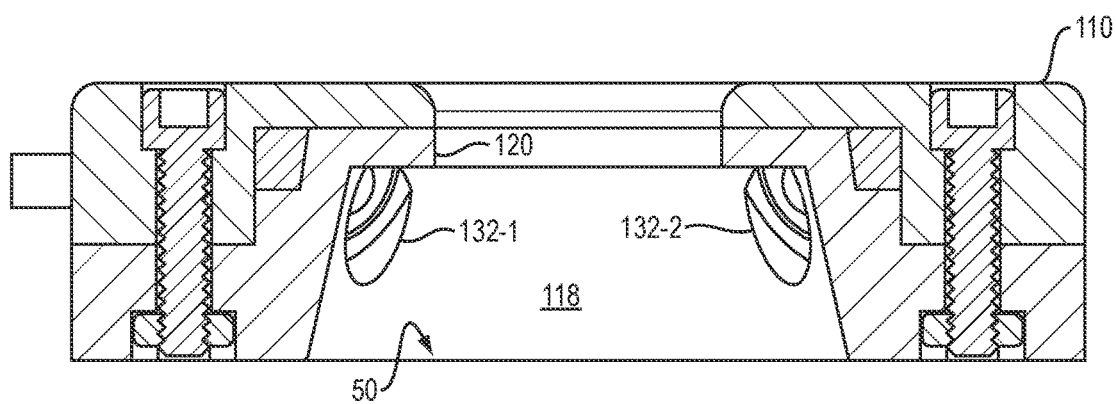
FIG. 6 shows a side, cutaway view of the central void and illumination cavity formed by the device of FIGS. 1-5.

FIG. 6 shows a side, cutaway view of the central void and light cavity formed by the device of FIGS. 1-5. Referring to FIGS. 1-6, a plurality of LED elements 132-1 . . . 132-2 (132 generally) surround the illumination cavity 118, although as few as 1 could be provided. In the example configuration, the plurality of LED elements 132 are disposed generally in a circle around the circumferential body 110, and fill the illumination cavity 118 with light focused on the treatment region 50. The inner surface of the circumferential body 110 and optional insert 121 are a light color and may be translucent to reflect and refract (distribute and target) as much if the light as possible around the illumination cavity 118 to fall on the treatment region 50. The antimicrobial light is therefore specifically targeted to fall on the treatment region defined by the percutaneous insertion and surrounding epidermal region, specifically within the illumination cavity 118 of the circumferential body 110.

Figure 7:
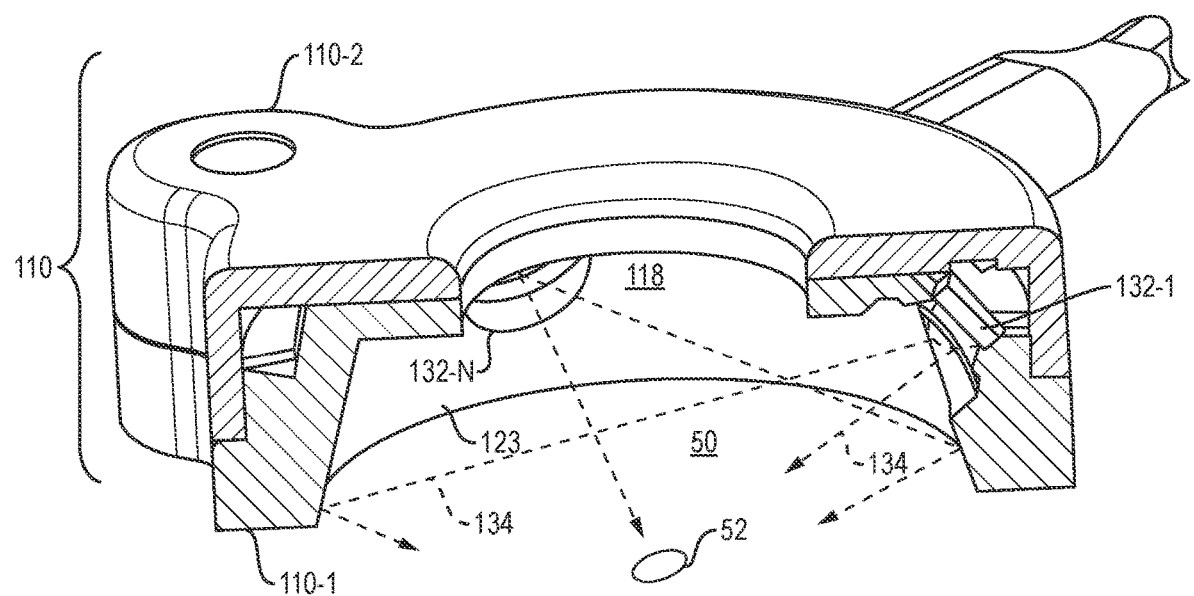
FIG. 7 shows a perspective view of the illumination cavity of FIG. 6.

FIG. 7 shows a perspective view of the light cavity of FIG. 6 as a cutaway from the circumferential body 110. Referring to FIGS. 1-7, the circumferential body 110 is disposed on a treatment region 50 and centered on or around an insertion site 52 of a percutaneous insertion member. One or more LED elements 132-N disposed on an inner surface 123 of the circumferential body bathe the illumination cavity 118 in light for directing the light directly on the treatment region 50 and also reflected and/or refracted around the inner surface 123 as shown by arrows 134. A light colored, translucent and/or reflective property of the inner surface 123 generally focuses direct and indirect light onto the treatment region 50 for eliminating harmful pathogens that may live on the skin surface around the insertion site 52.

Figure 8:
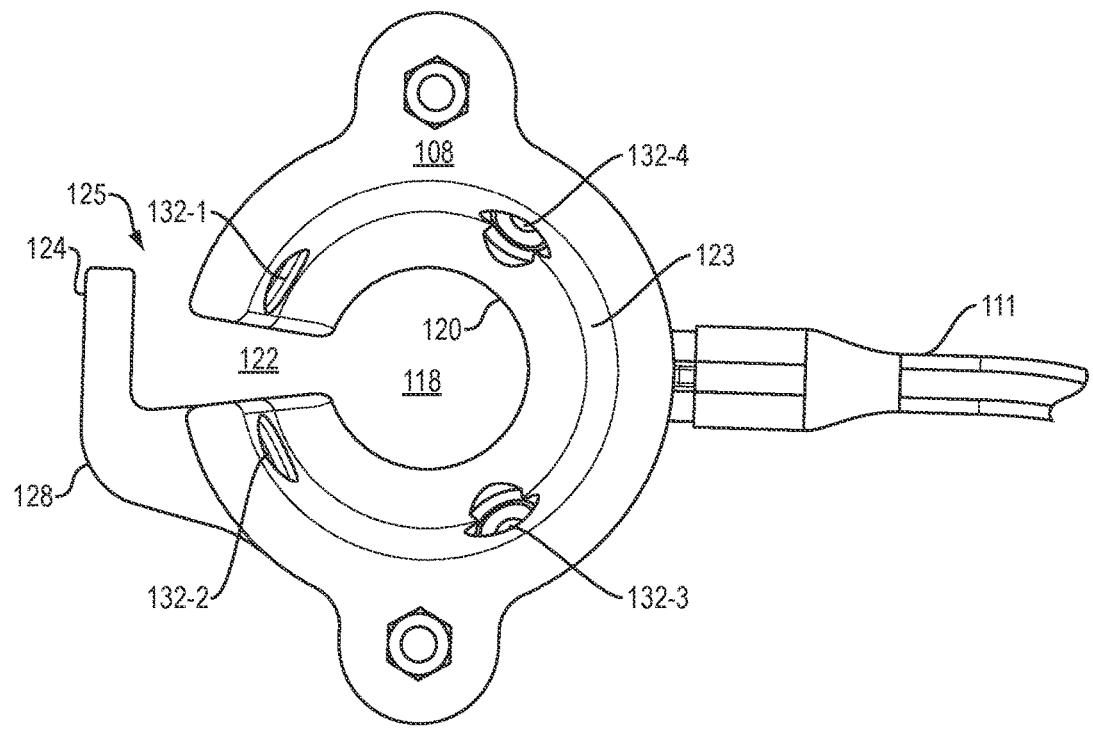
FIG. 8 shows a bottom view of the device of FIGS. 1-7.

FIG. 8 shows a bottom view of the device of FIGS. 1-7. Referring to FIGS. 7-8, FIG. 8 shows four LEDs 132-1 . . . 132-4 emanating from the inner surface 123, however any suitable number of LEDs may be provided based on the intensity and wavelength of the therapeutic light sought for irradiation. Any suitable propagated wavelength of the electromagnetic spectrum may be provided if an illumination element can be so equipped. The underside 108 rests on the dermal surface 10 at the treatment region, adhered by the adhesive member 116 as discussed above. The protrusion 124 has a bottom flush with the underside 128, and opens to define the illumination cavity 118. The lateral extension 128 is flush with the underside 128 for resting on the skin surface, and extends in an articulated manner for protrusion 124 to form the elevated surface 126 at the vessel gap 122.

Figure 9:
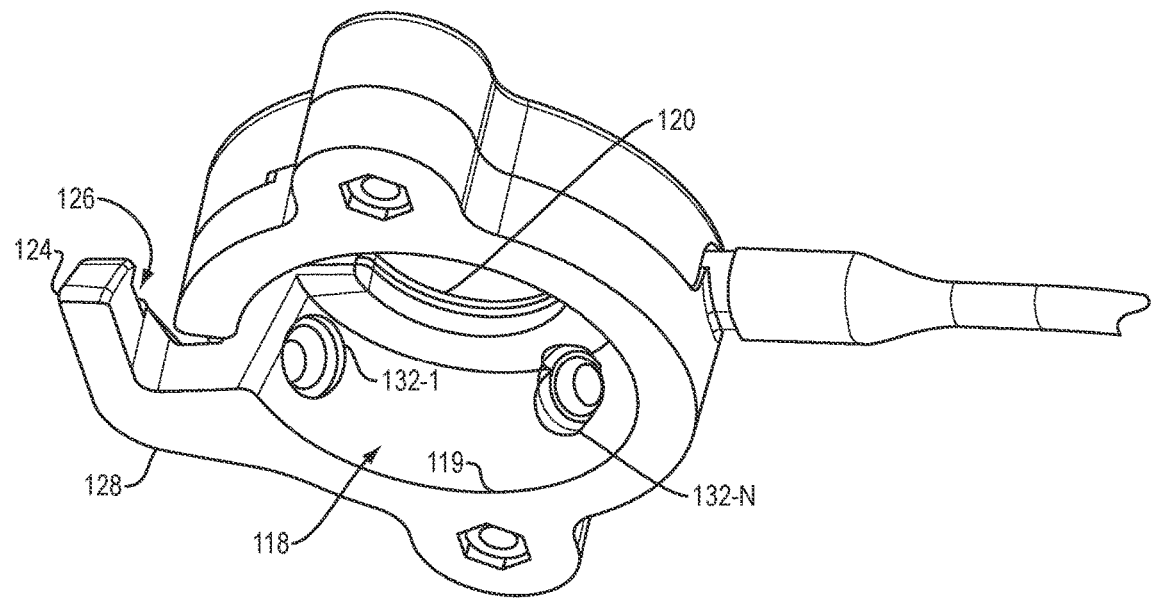
FIG. 9 shows an underside perspective view of the device and illumination/light cavity of FIGS. 6-8.

FIG. 9 shows an underside perspective view of the device and illumination cavity 118 of FIGS. 6-8. The illumination cavity 118 is based on a generally concave region under the central gap 120 and extending to an inner perimeter 119 of the circumferential body 110, with the vessel gap 122 allowing passage of the treatment vessel 140.

Figure 10:
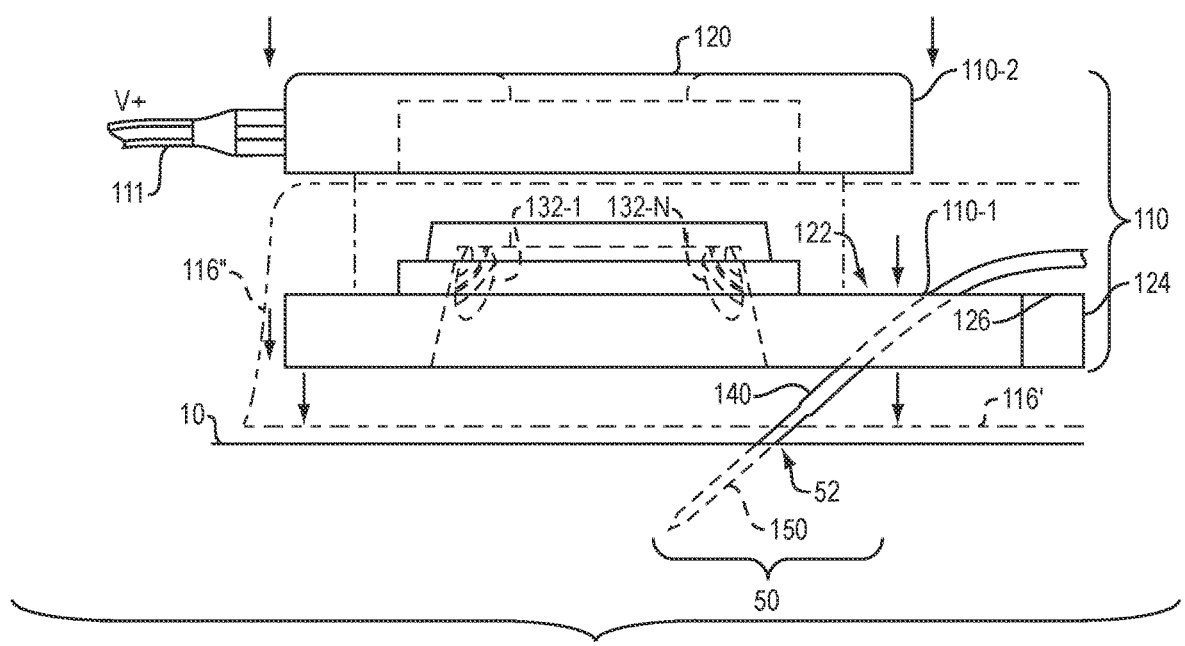
FIG. 10 shows a method of applying the antimicrobial light treatment of FIGS. 1-9.

FIG. 10 shows a method of applying the antimicrobial light treatment of FIGS. 1-9. Referring to FIGS. 1-10, a method for antimicrobial light treatment of a percutaneous insertion site as shown in FIG. 10 includes applying an adhesive member 116 to a treatment region 50 for securing a percutaneous insertion member in an insertion site. The percutaneous insertion member 150, such as a needle, is in fluidic communication with a medication vessel 140 for delivering medication, typically an IV line, infusion line or similar delivery system. The adhesive member 116 may adhere on the epidermal surface, shown as dotted line 116', or may be applied over the circumferential member 110, shown as dotted line 116". In the alternate configuration of FIGS. 3A-3B, the adhesive member 116" may reside between the proximate layer 110-1 and distal layer 110-2.

In either configuration, the circumferential body 110 is disposed onto the treatment region 52. The circumferential body 110 extends generally circular around a central void 120, and placement centers the central void around the insertion site so that the central void allows clearance for the medication vessel 140 and any uninserted portion of the rigid insertion member. The circumferential body 110 may be any suitable shape and size based on the treatment region 50 and the intensity of the illumination source 130 thereby irradiating the treatment region.

The circumferential body 110 includes a discontinuous portion defining the vessel gap 122, which may be continuous with the central void 120. In conjunction with placement of the circumferential body 110, the medication vessel is routed over the elevated surface 126 on the protrusion 124 extending from the circumferential body for permitting the vessel to extending through the vessel gap 122 above and out of contact with the skin surface. The treatment region 50 is illuminated from one or more LEDs (Light Emitting Diodes) 132 disposed on an inner surface of the circumferential body 110 for irradiating an illumination cavity 118 defined by the inner surface and the central void. The LEDs 132 or other illumination source irradiate the treatment region for maintaining an antimicrobial and sterile environment around the insertion site 50. This prevents pathogens from entering the patient along the insertion member 150.

In a particular configuration shown in FIGS. 3A-3C above, the circumferential body has multiple, engageable parts. A first, proximate layer 110-1 accompanies the insertion member 150. Disposing the circumferential body 110 further comprises disposing the proximate layer 110-1 by applying a proximate layer centered on the treatment region using the adhesive member 116, and engaging the distal layer 110-2 onto the proximate layer 116-1 by circumferentially aligning the distal layer with the proximate layer, the LEDs directed towards the illumination cavity. Any suitable adhesive, friction, interference and/or deformable (i.e. snap-fit plastic tab) mechanism may be employed for engaging the proximate 110-1 and distal 110-2 layers.

While the system and methods defined herein have been particularly shown and described with references to embodiments thereof, it will be understood by those skilled in the art that various changes in form and details may be made therein without departing from the scope of the invention encompassed by the appended claims.

What is claimed is:

1. A device, comprising:
    a light-emitting body configured for directing antimicrobial light at a percutaneous insertion site; and
    a central void in the light emitting body for unobstructed passage of a percutaneous device,
    the antimicrobial light defined by visible light for reducing an infection risk from a percutaneous medical device inserted at the insertion site.

2. The device of claim 1 wherein the light emitting body is configured for directing targeted antimicrobial light circumferentially at the percutaneous insertion site.

3. The device of claim 1 wherein the antimicrobial light is ultraviolet light for reducing an infection risk from a percutaneous medical device inserted at the insertion site.

4. The device of claim 1 wherein the light emitting body is configured for directing targeted antimicrobial light at the percutaneous insertion site.

5. The device of claim 1 wherein the light emitting body is configured for directing targeted ultraviolet and/or visible light at the percutaneous insertion site.

6. The device of claim 1 further comprising transparent dressing disposed between the light emitting body and the percutaneous insertion site.

7. An antimicrobial device, comprising:
    a body adapted for placement on a skin region around a percutaneous device;
    an illumination source on the body disposed for emitting antimicrobial light at a percutaneous insertion site; and
    a central void in the body for unobstructed passage of a percutaneous device, the antimicrobial light defined by visible light for reducing an infection risk from a percutaneous medical device inserted at the insertion site.

8. The device of claim 7 further comprising at least one LED element defining the illumination source, the LED element emitting an antimicrobial light.

9. The device of claim 8 wherein the body further comprises a distal layer including a power connection for powering the at least one LED element and a proximate layer, the proximate layer interfacing with an underlying dressing, skin, or antimicrobial agent.

10. The device of claim 7 further comprising a plurality of LED elements, the plurality of LED elements disposed around the body, each of the LED elements focused on the insertion site.

11. The device of claim 7 wherein the percutaneous insertion site is around the indwelling percutaneous device or instrument.

12. The device of claim 7 wherein the central void has a size based on a percutaneous device or instrument.

13. The device of claim 7 further comprising a power connection on the body, the power connection coupled to the illumination source and adapted for receiving an electrical source for powering the illumination source.

14. The device of claim 7 wherein the body is disposed on a skin surface, further comprising an adhesive member, the adhesive member having an adhesive attraction to the skin surface and extending over the treatment region and disposed for securing the body and a percutaneous device or instrument directed to a central void.

15. An antimicrobial device, comprising:
    a body adapted for placement on a skin surface around a percutaneous device; and
    an illumination source disposed for emitting antimicrobial light at a percutaneous insertion site,
    further comprising a discontinuity in the body, the discontinuity defining a gap for accommodating a percutaneous device or instrument.

16. The device of claim 15 further comprising a protrusion extending outward from the body, the protrusion having an elevated surface disposed away from the skin surface, the elevated surface adjacent the percutaneous device or gap for directing the percutaneous device or instrument at an offset distance from the skin surface.

17. An antimicrobial device, comprising:
    a body having a central void and adapted for placement on the skin around a percutaneous device; and
    an illumination source disposed for emitting antimicrobial light at a percutaneous insertion site, further comprising:
    a gap in the body;
    a lateral extension extending radially from the body adjacent the gap; and
    an elevated surface on the lateral extension, the elevated surface disposed on a path towards the central void for receiving a percutaneous device or instrument, the percutaneous device or instrument disposed on the path into the body through the percutaneous insertion site.

18. A method for reducing infection risk from percutaneous devices or instruments, comprising:
    targeting antimicrobial light at an insertion site,
    the antimicrobial light directed through a central void in a body for unobstructed passage of a percutaneous device,
    the antimicrobial light defined by visible light for reducing an infection risk from a percutaneous medical device inserted at the insertion site.

19. The method of claim 18, wherein targeting the antimicrobial light further comprises:
    disposing an antimicrobial light emitting body around the insertion site; and
    illuminating a treatment region from one or more LEDs disposed on an inner surface of the body for circumferentially irradiating percutaneous insertion site.

20. The method of claim 19 wherein disposing the body further comprises:
    disposing a proximate layer centered on the percutaneous insertion site comprising an underlying dressing, antimicrobial, or skin directly;
    activating the one or more LEDs, the LEDs disposed on a distal layer; and
    aligning the distal layer on the proximate layer, the LEDs directed towards the insertion site.

21. The method of claim 18 wherein the antimicrobial light comprises at least one of ultraviolet or visible spectrum light.

22. A system comprising:
    an antimicrobial light-emitting device; and
    an attachment disposed between the antimicrobial light-emitting device and a skin surface, wherein the attachment affixes the targeted antimicrobial light towards a percutaneous device insertion site;
    a central void in the light emitting device for unobstructed passage of a percutaneous device,
    the antimicrobial light defined by visible light for reducing an infection risk from a percutaneous medical device inserted at the percutaneous device insertion site.

23. The system of claim 22 wherein the attachment is a dressing.

24. The system of claim 23 wherein the attachment further comprises a securement or fixation dressing.

25. The system of claim 23 wherein the dressing is transparent.

26. The system of claim 23 wherein the dressing is antimicrobial.

27. A system comprising:
    an antimicrobial light-emitting device; and
    an attachment disposed between the antimicrobial light-emitting device and a skin surface, wherein the attachment affixes the antimicrobial light emitting device directed towards a percutaneous device insertion site on a dermal surface; and
    the attachment further comprising an elevated surface adjacent a percutaneous device or instrument for directing a percutaneous device or instrument at an offset distance from the dermal surface.

* * * * *